Figure 1:
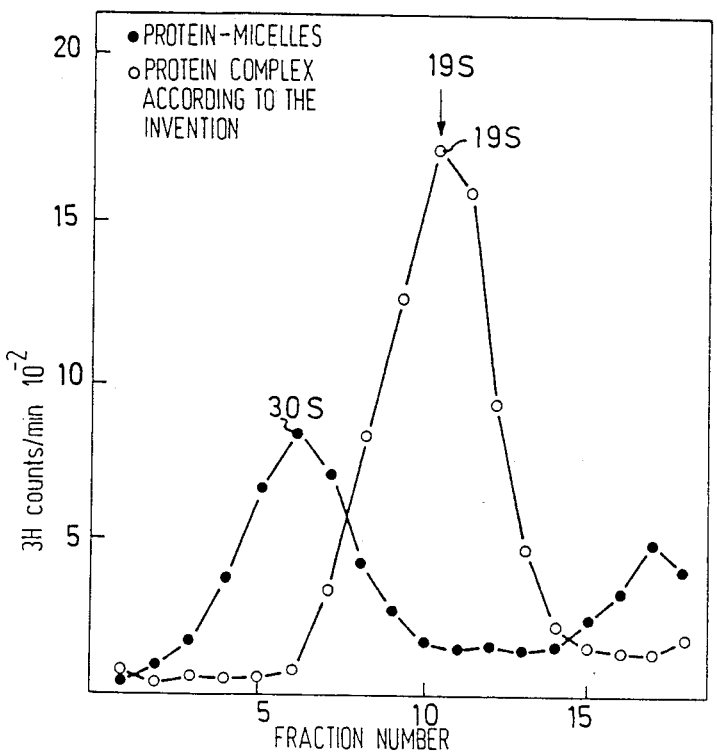

United States Patent [19]

Morein

[11] Patent Number: 4,744,983

[45] Date of Patent: * May 17, 1988

[54] IMMUNOGENIC PROTEIN OR PEPTIDE COMPLEX, METHOD OF PRODUCING SAID COMPLEX AND THE USE THEREOF AS AN IMMUNE STIMULANT AND AS A VACCINE

[76] Inventor: Bror Morein, Krokusvägen 14, S-175 74 Järfälla, Sweden

[*] Notice: The portion of the term of this patent subsequent to Mar. 25, 2003 has been disclaimed.

[21] Appl. No.: 825,778

[22] Filed: Jan. 31, 1986

Related U.S. Application Data

[62] Division of Ser. No. 543,032, Oct. 18, 1983, Pat. No. 4,578,269.

[30] Foreign Application Priority Data

Oct. 18, 1982 [SE] Sweden ................... 8205892

[51] Int. Cl.$^4$ .............. A61K 39/00; C07K 1/02; C07K 3/12; C07K 17/10
[52] U.S. Cl. ..................... 424/88; 530/300; 530/344; 530/350; 530/403; 530/406; 530/419; 530/423; 424/89; 424/92; 435/68; 435/172.2; 435/172.3
[58] Field of Search ............ 424/88, 89, 92; 530/403; 570/300, 344, 350, 403, 406, 419, 423, 806; 514/21

[56] References Cited

U.S. PATENT DOCUMENTS

| | | | |
|---|---|---|---|
| 4,053,585 | 10/1977 | Allison | 424/89 X |
| 4,064,232 | 12/1977 | Bachmayer | 424/89 |
| 4,117,113 | 9/1978 | Allison | 424/89 |
| 4,148,876 | 4/1979 | Almeida | 424/89 |
| 4,196,191 | 4/1980 | Almeida | 424/89 |
| 4,201,767 | 5/1980 | Fullerton | 424/89 |
| 4,235,877 | 11/1980 | Fullerton | 424/89 |
| 4,251,509 | 2/1981 | Hanson | 424/89 |
| 4,261,975 | 4/1981 | Fullerton | 424/89 |
| 4,356,169 | 10/1982 | Simons | 424/89 |
| 4,578,269 | 3/1986 | Morein | 424/88 |

FOREIGN PATENT DOCUMENTS

| | | |
|---|---|---|
| 37931 | 10/1981 | European Pat. Off. |
| 47480 | 3/1982 | European Pat. Off. |
| 58021 | 8/1982 | European Pat. Off. |
| 1083815 | 9/1967 | United Kingdom |

OTHER PUBLICATIONS

Chemical Abstracts, 176074p, vol. 81, p. 428, 1974.
Arch. Gasamte Virusforsch, 1974, 44 (3), 243-254, Dalsgaard.

Primary Examiner—Howard E. Schain
Attorney, Agent, or Firm—Young & Thompson

[57] ABSTRACT

The invention relates to an immunogenic complex containing antigenic membrane proteins or peptides from viruses mycoplasmas, bacteria, parasites or animal cells or prepared synthetically or with hybride DNA technique and glycoside. The invention also relates to a process for producing the complex, whereby microorganisms, animal cells, proteins and peptides are mixed with solubilizing agents in buffered, possibly saline, solution, whereby complexes are formed between charged monomeric antigenic proteins and detergent or peptides and solubilizing agents, whereafter the charged monomeric antigenic proteins or peptides are separated from solubilizing agents in the presence of, or are separated from solubilizing agent and directly transferred to, a glycoside solution which contains one or more glycosides with hydrophobic and hydrophilic regions in a concentration of at least the critical micellular concentration, whereby a protein complex is formed, which is isolated and purified. The invention also relates to the use of the immunogenic complex as an immunity-stimulating agent, especially as a vaccine, and compositions containing the complex.

8 Claims, 3 Drawing Sheets

IMMUNOGENIC PROTEIN OR PEPTIDE COMPLEX, METHOD OF PRODUCING SAID COMPLEX AND THE USE THEREOF AS AN IMMUNE STIMULANT AND AS A VACCINE

This application is a division of application Ser. No. 543,032, filed 10-18-83, now U.S. Pat. No. 4,578,269.

The present invention relates to an immunogenic complex, so-called iscom, between antigenic proteins and peptides from viruses, mycoplasmas, bacteria, parasites or animal cells. The invention also relates to a process for production thereof and the use thereof as an immune stimulant and vaccine.

It is known that killed viruses for example influenza virus, have a good antigenic effect. They are, however, pyrogenic even after extensive purification. By isolation of components which are important for induction of protective immunity, the pyrogenic effect has been avoided, but the immunogenicity is often not sufficiently strong. Therefore suitable adjuvants must be introduced in those vaccines containing the isolated antigens (subunits) in order to increase the immune response. On the other hand, effective adjuvants cause, in the manner which they have been used up to now, negative side effects. Adjuvant-containing vaccines are thus no better than vaccines based on the entire virus, as regards the pyrogenic effect.

In order to increase the immunogenicity, detergent membrane proteins have been produced, which have been entrapped or bound to the surface of liposomes (EPC Application No. 7940083.0). Detergent-free membrane proteins in liposomes are described in U.S. Pat. No. 4,148,876. Incorporation of adjuvants in such detergent-free unilamellar liposome products is mentioned in U.S. Pat. No. 4,196,191 (without reporting on the effect thereof). U.S. Pat. No. 4,117,113 describes negatively charged liposomes containing virus antigen. In such liposomes containing influenza haemagglutinin and neuraminidase, incorporation in liposomes of an adjuvant, mycobacterial cell walls, produces a better immune response. Better immune responses have also been obtained when adjuvants such as killed *Mycobacterium tuberculosis, Bordetella pertussis* and saponins have been introduced in such negatively charged liposomes containing diphtheria toxoid (U.S. Pat. No. 4,053,585). All of the above-mentioned lipid-containing membrane protein products are, however, unstable after long storage, freeze-drying or uncareful handling, e.g. high temperature.

Detergent-free and lipid-free protein micelles have also been produced as vaccine. It has been demonstrated that micelles of membrane proteins of Semliki Forest Virus (SFV) stimulate the formation of circulating antibodies against SFV and produce a protection in mice against fatal infection by SFV. On the other hand, such membrane protein micelles of parainfluenza-3-virus were not effective for stimulating antibody formation in lambs or in protecting against a dose of PI-3-culture causing pneumonia, if an oil adjuvant was not mixed with the micelles. Oil adjuvants usually produce side effects in the form of local reactions at the infection site (EPC Application No. 81102213.6).

The purpose of the present invention is to avoid these disadvantages and to achieve a storage-stable protein complex with high immunogenicity and without side effects. This is achieved with lipid-free complexes between hydrophobic regions in proteins and peptides from viruses, mycoplasmas bacteria, animal cells or parasites, said complexes being produced by the addition of one or more glycosides. The new complexes have another morphological structure under electron microscopy than corresponding protein micelles produced without the addition of glycosides. The micelles have a compact central core with radially arranged spikes, while the complex according to the invention has an open spherical structure consisting of circular subunits or parts of the spheric structure. The complexes and the parts thereof also usually have a lower sedimentation constant (see FIG. 1) than corresponding micelles and a higher sedimentation constant than the corresponding monomeric form of protein or peptide.

The complexes according to the invention, which have been produced with the addition of glycosides, have better immunogenic activity than corresponding protein micelles produced without the addition of glycoside or complex between a protein molecule and solubilizing agent (monomeric forms) or protein molecules bound to a lipide i.e. virosomes and produce fewer side effects than when the protein micelles are mixed with the glycosides or other adjuvants. Thus the dose of membrane proteins can be reduced to about 1/10 or more.

The proteins or peptides with hydrophobic regions that are complexed to hydrophobic regions of the glycosides may be (A) amphiphatic proteins or peptides with hydrophilic and hydrophobic groups derived from or being membrane proteins or membrane peptides from enveloped viruses, bacteria, mycoplasmas, parasites or animal cells, or such proteins or peptides produced by hybrid DNA technique, or molecules produced synthetically, (B) hydrophilic proteins or peptides made amphiphatic by hydrophobic groups being coupled to them. These proteins or peptides may derive from viruses, bacteria, mycoplasmas, parasites, or be synthesized or obtained by hybrid DNA technique, (C) amphiphatic proteins or peptides obtained by inaccessible hydrophobic parts of hydrophilic proteins being made accessible by chemical means. These proteins may derive from the microorganisms or cells mentioned above or obtained by hybrid DNA technique, or be synthesized.

Preparation of complex (a) Concerning the preparation of membrane proteins or membrane peptides derived from whole cells or viruses, the preparation of the complexes comprises in principle three steps: purification or isolation of animal cells or microorganisms or fragments thereof; solubilizing of hydrophobic proteins and removal of the solubilizing agent while at the same time transferring the desired antigen in complex by means of glycoside in an immunogenic form (immunogenic complex).

Purification and isolation

Viruses, mycoplasmas bacteria, parasites and animal cells are concentrated and purified in a known manner (for references see "The Tools of Biochemistry", T G Cooper, John Wiley & Sons (1977) New York, which is incorporated as a reference) for example by gel filtration or centrifuging through a sugar gradient or gradient centrifuging through percoll or with hollow fiber dialysis. For bacteria, it can be necessary or more advantageous to first lyse or break down the cell walls (for references see Cota-Robles and Stein, CRC Handbook of Microbiology Vol II (1973) pp 833-844 which is incorporated as a reference) with ultrasond or French press treatment for example.

Solubilizing

The purified animal cells or microorganisms or fragments thereof are then mixed with non-ionic, ionic or Zwitterionic detergent or detergent based on gallic acid which is used in excess. Typical examples of suitable non-ionic detergents are polyglycol esters and polyglycol ethers with aliphatic or aralylphatic acids and alcohols. Examples of these are alkylpolyoxyethylene ethers with the general formula $C_nH_{2n+1}(OCH_2CH_2)_xOH$, shortened to $C_nE_x$; alkylphenyl polyoxyethylene ethers containing a phenyl ring between the alkyl group and the polyoxyethylene chain, abbreviated $C_n\phi E_x$, e.g. Triton X-100=tert.-$C_8E_{9,6}$ (octylphenolether of polyethylene oxide), acylpolyoxyethylene esters; acylpolyoxyethylene sorbitane esters, abbreviated $C_n$ sorbitane $E_x$, e.g. Tween 20, Tween 80, $\beta$-D-alkylglucosides, e.g. $\beta$-D-octylglucoside. The glycosides mentioned below can also be used, especially saponin. These are, however, weak detergents and should be used together with other detergents. Typical examples of suitable ionic detergents are gallic acid detergents such as e.g. desoxycholate and cholate. Even conjugated detergents such as e.g. taurodeoxycholate, glycodeoxycholate and glycocholate can be used. Possible Zwitterionic detergents are lysolecitin and synthetic lysophospholipids. Even mixtures of the above-mentioned detergents can be used.

Solubilizing can also be performed with alcohols, organic solvents or small amphiphatic molecules such as heptane-1,2,3-triol, hexane-1,2,3-triol, acetic acid, water-soluble peptides and proteins or mixtures thereof, or with detergents.

The solubilizing agent is used in excess in relation to the amount of lipid and hydrophobic proteins. Suitably cells or microorganisms and detergent are mixed in the weight ratio 1:3 to 1:10.

Cells or microorganisms and solubilizing agent are mixed in buffered possibly saline solution. The molarity of the saline solution lies between 0.02 and 0.5M, preferably between 0.05 and 0.25M. 0.1-0.2M is preferred. The detergent should act for about 1 hour at room temperature.

Sodium chloride is preferred as a salt, but other salts can also be considered, especially salts with alkali ions, earth alkali ions and ammonium ions and strong mineral acids and organic acids such as acetic acid, trichloroacidic acid, formic acid and oxalic acid. As a buffer, all substances are suitable which buffer in the pH interval 6.5-9. When using cholates and desoxycholates, pH 8-9 is preferred, and when using non-ionic detergents, pH 7.4.

The preparation of immunogenic complexes

When cells or microorganisms have been solubilized, a mixture of solubilizing agent and cell or microorganism fragments are formed (hereinafter called fragments). Among the fragments there are charged monomeric antigenic proteins with hydrophobic regions in complex with the solubilizing agent. The new immunogenic complex according to the invention is produced by separating the charged monomeric antigenic proteins from the solubilizing agent in the presence of, or by directly transferring to, one or more glycosides which must have hydrophobic and hydrophilic regions and be present in a concentration of at least the critical micelle concentration. The rest of the fragments are removed before the complex according to the invention is produced, while it is being produced, or afterwards, preferably before.

The complex according to the invention can be produced either by removing the solubilizing agent, e.g. by dialysis, gel filtration or chromatography from the mixture of solubilizing agent, charged monomeric antigenic proteins, glycoside and possibly other fragments or by separating the charged, monomeric, antigenic proteins from said mixture, e.g. by gradient centrifuging, chromatography or electrophoresis. The essential feature of the invention is that the monomeric antigenic proteins are separated from the solubilizing agent during the simultaneous presence of the glycoside or after separation are directly transferred to the glycoside, of which the micelle form should be present. When the monomeric antigenic proteins are separated from the solubilizing agent so that they can come directly into contact with the glycoside, the special complex according to the invention is formed. It is assumed that the micelle form of the glycoside is the base for forming the complex and that this is formed by attraction between hydrophobic regions on the glycoside micelles and hydrophobic regions on the membrane proteins. The amount of glycoside in the complex varies depending on the glycoside used and the complex bound membrane proteins and lies between 0.5 and 50% by weight, especially between 0.5 and 25% by weight, preferably between 0.5 and 15, often between 0.5 and 10% by weight, and especially between 2 and 8% by weight. If the charged antigenic monomeric proteins are separated from the solubilizing agent in the absence of the glycoside, protein micelles of the type produced according to EPC Application No. 81102213.6 are formed however.

It is suitable to remove the other fragments by gradient centrifuging since the sedimentation constant for the components involved decreases in the following order: cell fragment, protein complex with solubilizing agent or according to the invention, monomeric proteins and solubilizing agent. Thus the other fragments can be removed with gradient centrifuging from the mixture of solubilizing agent, monomeric proteins, and other fragments before the glycoside is added and the solubilizing agent removed, e.g. by dialysis, gel filtration, chromatography or the monomeric proteins can be separated from the solubilizing agent, e.g. by electrophoresis, chromatography or gradient centrifuging. In the latter method, it is also possible to remove the other fragments during the same gradient centrifuging, as the complex is formed. It is also possible to separate other cell components after the complex has been formed according to the above, e.g. by centrifuging, affinity chromatography, or gel filtration.

The glycoside can be any glycoside at all with hydrophobic and hydrophilic regions. Preferably, the saponins are used which are described in R Tschesche and Wulf, Chemie und Biologie der Saponine in Fortschritte der Chemie Organischer Naturstoffe, published by W Herz, H Grisebach, G W Kirby, Vol 30 (1973), especially the strongly polar saponins, primarily the polar triterpensaponins such as the polar acidic bisdesmosides, e.g. saponin extract from Quillajabark Araloside A, Chikosetsusaponin IV, Calendula-Glycoside C, Chikusetsusaponin V, Achyranthes-Saponin B, Calendula-Glycoside A, Araloside B, Araloside C, Putranjia-Saponin III, Bersamasaponoside, Putranjia-Saponin IV, Trichoside A, Trichoside B, Saponaside A, Trichoside C, Gypsoside, Nutanoside, Dianthoside C, Saponaside D, preferably aescine from *Aesculus hippocastanum* (T Patt and W Winkler: Das therapeutisch wirksame Prinzip der Rosskastanie (*Aesculus hippocastanum*), Arzneimittelforschung 10 (4), 273-275 (1960) or sapoalbin from *Gypsophilla struthium* (R Vochten, P Joos and R Ruyssen: Physicochemical properties of sapoalbin and their relation to the foam stability, J Pharm Belg 42, 213-226 (1968), especially saponin extract from *Quillaja saponaria Molina*, primarily the DQ-extract which is produced according to K Dalsgaard: Saponin Adjuvants, Bull Off Int Epiz 77 (7-8), 1289-1295 (1972) and Quil A which is produced according to K Dalsgaard: Saponin Adjuvants III, Archiv für die Gesamte Virusforschung 44, 243-254 (1974). Also mixtures of glycosides can be used. The amount of glycoside added should be at least 1-3 times their critical micelle formation concentration (CMC), preferably at least 5, especially at least 7-12 times. It is assumed that the glycoside in this case can be bound to and catch monomer forms of the membrane proteins. Preferably Quil A is used, which has a critical micelle formation concentration of 0.03% by weight. The amount of Quil A should then be at least 0.02% by weight, especially 0.05-0.5% by weight, preferably 0.2% by weight. The citations above concerning the glycosides are incorporated as references.

The separation of the charged monomeric antigenic proteins from the solubilizing agent has been done by centrifuging, dialysis electrophoresis, and different chromatographic methods.

The centrifuge method

The mixture of fragmented cells or microorganisms and solubilizing agent made according to the above is gradient-centrifuged and layered on top of e.g. a sugar or salt solution, containing solubilizing agent, under which a gradient containing the glycoside is present, such as a sugar gradient or a gradient of glycerol or metrize amide or a heavy salt, e.g. CsCl (i.e. relatively inert substances which have suitable density, viscosity to act as gradient material), e.g. with the concentrations for a sugar gradient given below.

The gradient system is centrifuged at at least 100,000 g. As sugar there can be used monosaccharides such as, lactose, maltose, disaccharides such as lactose, maltose, saccharose, but also trioses, tetroses and glycerine. Preferably saccharose is used. The sugar concentration in the gradient is suitably at least 5, preferably 15-25% by weight as beginning concentration (uppermost in the gradient) and the final concentration is at least 20, preferably 45-60% by weight (lowermost in the gradient). The gradient can for example consist of an upper layer with 5-25% by weight sugar content and a lower layer with 20-60% by weight sugar content. However, there can also be several layers, the concentration differences between the individual layers being reduced correspondingly. The sugar gradient contains a glycoside or a mixture of glycosides. The amount of glycoside should be at least 1-3, preferably at least 7-12 times CMC for Quil A at least 0.02, especially at least 0.05-0.5, preferably at least 0.2% by weight. In this glycoside containing gradient the solubilizing agent is separated, and the complex between the solubilizing agent and the protein is transformed to protein-glycoside complex.

On top of the sugar gradient there is a layer of a solution of sugar or heavy salt which contains solubilizing agent or a mixture of solubilizing agents. The lipids are remaining in this layer. The concentration of solubilizing agent in this layer is less than or the same as in the applied mixture of microorganisms or cells and solubilizing agent and lies suitably between 0.12 and 3% by weight, preferably between 0.75 and 1.5% by weight, with 1% by weight being preferred. The sugar or salt concentration can be the same as or less than the concentration in the upper layer of the gradient.

After centrifuging at at least 100,000 g for at least 16 h, preferably for 20 h at 20° C., the proteinaceous fractions are collected and dialyzed against buffer (0.5M to 0.001M) preferably 0.005M Tris-HCl, 0.01M NaCl, pH 7.4 or 0.2M ammonium acetate buffer, pH 7.0 and is concentrated e.g. as described in The Tools of Biochemistry by T G Cooper, edit John Wiley & Sons (New York 1974) which is incorporated as a reference, e.g. by lyophilisation, vacuum dialysis and ultrafiltrating. During the centrifuging, all constituents are settling whereby the solubilizing agent loosens from the complex of protein and solubilizing agent, and the monomeric proteins are transferred to the glycoside and form complexes therewith. In the subsequent dialysis the sugar is taken away.

The complex can possibly be purified further, e.g. from free glycoside by gradient centrifuging, e.g. by a sugar gradient containing 25-60% by weight sugar, preferably 10-40% by weight saccharose.

The dialysis method

After purification of cells or the microorganisms as described above and after they have been mixed with solubilizing agent in the above described weight ratio, the mixture of cells and solubilizing agent, in the above described buffer can alternatively directly be mixed with at least 1-3, preferably 7-12 times CMC for Quil A 0.05-2% by weight glycoside, preferably 0.2% by weight glycoside and be dialyzed against the buffer such as 0.5-0.001M, preferably 0.005M Tris-HCl, 0.01M NaCl, pH 7.4, especially 0.2M ammonium acetate buffer, pH 7.0. This separates the solubilizing agent in the presence of the glycoside. The membrane protein complex produced can then be isolated with sedimentation gradient centrifuging, such as is described on page 9, last paragraph, the glycoside additive is excluded however, and is freed from the other fragments and free glycoside.

The mixture of cells and microorganisms and solubilizing agent in buffer can also be gradient centrifuged and e.g. be layered on a 5-60% by weight sugar gradient in the above buffer, preferably a 10-20% by weight saccharose gradient and be centrifuged at at least 150,000 g for at least 20 minutes, preferably for 30 minutes at 250,000 g. The other fragments are thereby separated from the complex between solubilizing agent and protein.

The proteinaceous upper liquid, called top fraction, is extracted and the glycoside is added in an amount of at least 1-3, preferably at least 7-12 times CMC for Quil A 0.05-0.5% by weight, preferably 0.2% by weight, and is dialyzed against buffer 0.5-0.001M, especially 0.005M Tris-HCl, 0.01M HCl, pH 7.4, preferably 0.2M ammonium acetate. The solubilizing agent is removed in the presence of the glycoside. Further purification can be done with sedimentation gradient centrifuging (see page 9, last paragraph). Further purification can be done by centrifuging through a sugar gradient containing 5-60% by weight sugar, preferably 19-40% by weight sugar.

The electrophoresis method

Alternatively, the mixture of fragmented microorganisms or cells and solubilizing agent or the proteinaceous top liquid (other fragments and free solubilizing agent removed) which is obtained, when the mixture is gradient-centrifuged e.g. by a 5-60% by weight, preferably 10-20% by weight sugar gradient in buffer, is separated by electrophoresis from the solubilizing agent and is transferred in a solution containing at least 1-3, preferably at least 7-12 times CMC, for Quil A 0.05-0.5% by weight glycosides, preferably 0.2% by weight glycoside. The charged monomeric antigenic proteins are thereby separated from the solubilizing agent. For separation by electrophoresis, it is suitable that the solubilizing agent-buffer solution not contain extra added salt which can interfere with the electrophoresis and produce excessively high temperature. It is possible to use e.g. zone electrophoresis with or without carriers and isotakophoresis with or without carriers. Common substances can be used as carriers such as polyacrylamide, agar, silica gel, starch, cellulose, polyvinylchloride, ion exchanger, celite. Isolation and concentration of complexes are done as described on page 10, lines 23-26. Further purification with gradient-centrifuging (see page 10, last paragraph).

If hydrophobic membrane proteins with various charges or weight are present in the starting material, it is possible with electrophoresis or the centrifuging methods to separate them from each other and produce separate complexes of them. With these conditions, it is possible to separate and enrich complexes of various membrane proteins.

Chromatographic methods

The solubilized proteins can optionally, after being purified from cell fragments, be separated from the solubilizing agent with chromatographic methods e.g. gel-filtration, the antigen structure being adsorbed into an insoluble substratum (matrix) which may consist of e.g. cellulose, agarose, dextrane, acrylamide and glass. Different ligands are coupled to the matrix structure which then receives specific properties which are utilized during the separation. The antigen structure is usually adsorbed at the same time as the solubilizing agent used passes unadsorbed through the matrix. Then follows desadsorbation of the antigen. Before or during the desadsorbation step there can take place an exchange of solubilizing agent, salt and buffer substance, the solubilizing agent being replaceable by the glycoside, and complex being formed.

In ion exchange chromatography, charged ligand molecules such as diethylaminoethyl (DEAE) are coupled to matrix and employed as cation exchangers. Carboxyl methyl (CM) or phosphate groups (P) are coupled to matrix and employed as anion exchangers. By using differences in net charge between antigen structures and solubilizing agent, these molecules are separated. In general the solubilizing agent is uncharged and the protein charged. Elution is performed with salt gradient such as K- or NaCl- or pH adjustment with a suitable buffer, e.g. phosphates in the presence of a solubilizing agent (as to concentration and examples see section Solubilizing above). In elution the protein can be purified, the solubilizing agent exchanged or the complex formed if the glycoside is added to the eluant instead of solubilizing agent. Salts are subsequently removed by dialysis or gel-filtration.

Gel filtration makes use of the solubilizing agent being smaller than the antigen structures and coming out in subsequent fractions. Upon complex formation the size of the antigen-containing structures increases and they migrate from the detergent-containing zone.

By means of immunoaffinity-chromatography antibodies can be irreversibly bonded to the matrix mentioned above, whereafter the unique specificity and affinity of antibodies are utilized for purifying the desired antigen structure. The solubilizing agent has no affinity for antibodies. Elution is performed by mild denaturation, e.g. pH reduction to about 4 and in the presence of solubilizing agent or glycoside.

In lectin chromatography are used lectins, a group of proteins capable of reacting reversibly with specific sugar groups, which makes it possible for them to bind glycoproteins, for example. The lectin is coupled as ligand to e.g. Sepharose (Pharmacia, Uppsala) or is commercially bought ready-coupled to a suitable matrix. Detergents (solubilizing agents) have no affinity for the immobilized lectin. The adsorbed antigen structure is usually desadsorbed by addition of methylated sugar such as methyl mannoside, methyl glucoside and N-acetylglycosamine dissolved in buffered salt solution in the presence of solubilizing agent or glycoside.

In covalent chromatography, an antigen structure with a thiol group with a covalent bond is bonded to matrix. The thiol group in the antigen is selectively bonded to an activated thio group coupled to a suitable matrix by thio-disulfide exchange. This bond is reversible, and after removal by washing of the solubilizing agent the thiol-carrying antigen structure can be eluted by reduction of the disulphide bond by mercapto ethanol or dithiotrietol in the presence of solubilizing agent or glycoside.

Hydrophobic chromatography

This technique employs the interaction of an immobilized hydrophobic ligand of the octyl, phenyl type and hydrophobic surfaces of the antigen structure. Alternatively, this technique can be a method of bonding the solubilizing agent from the mixture to the ligand at the same time as the antigen structure can unadsorbed be recovered for continued treatment according to Example 4 (the dialysis method). Under other conditions the antigen structure can be bonded to the ligand, and as the solubilizing agent has no affinity for the ligand, one proceeds according to the dialysis method. Immobilization at high ion strength is effected by e.g. ammonium sulphate, and elution is effected at low ion strength with water or ethylene glycol.

The complexes can thus contain membrane proteins from bacteria, it being then advantageous to first break the cell walls before the cell material is treated by the process above. Examples of bacteria from which hydrophobic proteins can be produced are e.g. Escherichia, Staphylococci, Haemaophilus, e.g. *H. influenzae*, Bordetella, e.g. *B. pertussis*, Vibrio, e.g. *V. cholerae*, Salmonella, e.g. *S. typhi, S. paratyphi*, preferably adherence facter in Coli, e.g. pili K 88 and porin protein in e.g. Salmonella or outer membrane proteins from *B. pertussis* and *Neisseria meningitidis*.

Examples of usable viruses with envelopes are Orthomyxoviridae such as influenza A,B,C, Paramyxoviridae, especially measles virus, mumps virus, parainfluenza 1,2,3 and 4.viruses, canine distemper virus and rinderpest virus, Rhabdoviridae, especially rabies virus, Retroviridae, especially feline leukemia virus and bovine leukemia virus, Herpesviridae, especially Pseudorabies, Coronaviridae, Togaviridae, such as EEE,-WEE,VEE (eastern, western and Venezuela equine encephalitis), yellow feaver virus, especially bovine virus diarrhea virus, and European swine feaver virus Arenaviridae, Poxviridae, Bunyaviridae, Iridioviridae, especially African swine feaver virus and among unclassified viruses, human hepatitis B-virus and Marburg-/Ebola virus.

Examples of parasites which can be used according to the invention are Protoza, such as Toxoplasma, e.g. *Toxoplasma gondii*, Plasmodium, e.g. *Plasmodium vivax, malariae, falciparium, Teileria parvum ovale* and Filaroidae, preferably Parafilaria and Onchocerca, *Entamoeba histolytica*, anaplasma of various types, Schistosoma such as *Schistosoma haematobium, mansoni, japonicum*, and Trypanosoma, e.g. *Trypanosoma gambiense, brusei* or *congolesi*.

(b) It is also possible to start from non-membrane hydrophobic proteins or from non-hydrophobic proteins or peptides. Non-hydrophobic proteins or pepetides may be rendered hydrophobic by coupling hydrophobic groups to them. Proteins as mentioned above may be derived from viruses with or without envelope, bacteria, mycoplasma, parasites. Examples of non-enveloped viruses with non-hydrophobic proteins are Picornaviridae, e.g. hoof-and-mouth disease virus, polio virus, Adenoviridae, Parvoviridae, e.g. feline pest virus and swine parvovirus, Reoviridae, e.g. Rotavirus. Examples of mycoplasma are *M. pnemoniae, mycoides, bovis, suis, orale, salvarium, hominis* and *fermentans*.

These proteins or peptides can be obtained purified such as described in (a).

The hydrophobic group that can be coupled to the non-hydrophobic proteins are straight, branched, saturated or unsaturated aliphatic chains having 1, 2, 3, 4, 5, 6, 7 and 8 carbon atoms, preferably 6, 7 and 8 carbon atoms; small peptides with 1, 2, 3, 4 or 5 amino acids, preferably 2, 3, 4, selected from Trp, Ile, Phe, Pro, Tyr, Leu, Var, especially Tyr; cholesterol derivatives such as choline acid, ursodesoxycholine acid.

These hydrophobic groups must be bonded to a group that can be coupled to the non-hydrophobic protein such as carboxyl-, amino-, disulphide-, hydroxyl-, sulphydryl- and carbonyl group, such as aldehyde groups.

As hydrophobic groups that can be coupled are selected preferably carboxyl, aldehyde, amino, hydroxyl, and disulphide derivatives of methan, ethane, propane, butane, hexane, heptane, octane and peptides containing Cys, Asp, Glu, Lys, preferably octanal and Tyr.Tyr.-Tyr-Cys, -Asp or -Glu. The hydrophobic groups with a group that can be coupled must be dissolved in water with the aid of for example the solubilizing agents and detergents mentioned above or hydrochloric acid, acetic acid, 67% by volume acetic acid, caustic liquor, ammonia, depending on what substance is to be dissolved. pH is then adjusted to the neutral direction without the substance precipitating; here it is to make sure that there is not obtained a pH value that denaturates the protein to which the hydrophobic group is to be coupled.

The hydrophobic molecule is added to the non-hydrophobic protein in the molar ratio of 10:1 to 0.1:1, preferably 1:1.

Hydrophobic groups with a carboxyl group as coupling molecule can be coupled to the protein through water-soluble carbodiimides or composite anhydrides. In the first case the carboxyl group is activated at pH 5 with carbodiimide and mixed with the protein dissolved in buffer pH 8 with a high phosphate content. In the latter case the carboxy compound is reacted with isobutylchloroformate in the presence of triethylamine in dioxane or acetonitrile, and the resulting anhydride is added to the protein at pH 8 to 9. It is also possible to convert the carboxyl group with hydrazine to hydrazide which together with aldehydes and ketones in periodate-oxidized sugar units in the protein gives hydrazone bonds.

The amino groups with nitrious acid can at a low temperature be converted to diazonium salts, which gives azo bonds with Tyr, His and Lys.

The hydroxyl groups with succinic anhydride can be converted to hemisuccinate derivatives which can be coupled as carboxyl groups.

Aldehyde groups can be reacted with amino groups in the protein to a Schiff's base.

Several coupling groups and methods are described in Journal of Immunological Methods, 59 (1983) 129–143, 289–299, Methods in Enzymology Vol 93 pp 280-33, and in Analytical Biochemistry 116, 402–407 (1981) which are here incorporated as references.

The proteins or peptides so produced having received hydrophobic groups are then complex-bonded with glycoside, as described in (a), but here the purification steps for removing cell fragments can be omitted.

(c) It is also possible to start from hydrophilic proteins having enclosed hydrophobic groups and make them subsequently accessible by gently denaturating the proteins, i.e. with a low pH of about 2.5, 3M urea or at a high temperature above 70° C. Such proteins may be immunoglobulines such as IgG, IgM, IgA, IgD and Ig E. The immunoglobulines can be used as antidiotypic antibodies. The proteins are obtained purified as proteins as described in (b) and then complex-bonded to glycoside as described in (a), the purification steps for removing cell fragments being omitted.

The immunogenic complex according to the invention can be used for specific immuno-stimulation in humans and animals. They can thus be used as vaccines against deceases caused by bacteria, viruses, mycoplasmas and parasites and for producing antibodies for research purposes against membrane proteins from various animal cells.

Also mixtures of amphiphatic proteins from various bacteria or viruses can be added to produce vaccines against several afflictions.

The invention also concerns human or veterinary compositions comprising iscom according to the invention possibly together with usual additives and fillers preferably in the form of a buffer solution of iscom, i.e a T,N-solution (Example 1).

The invention will be described in more detail with the following nonlimiting examples.

EXAMPLE 1

Parainfluenza-3-virus U23 isolated in Umea, was purified by means of centrifuging through 30% by weight saccharose at 100,000 g for 1 hour at 4° C. The bottom layer was dissolved to a concentration of about 10 mg/ml in 0.05M Tris-HCl, pH 7.4 and 0.1M NaCl (TN). 1–5 mg/ml PI-3-virus in the same buffer (TN) was solubilized with 2% by weight (final concentration) Triton X-100 together with about $10^5$ counts/minute $^3$H-marked virus (A Luukkonen, C Gamberg, E Renkonen (1979) Virology 76 pp 55–59, which is incorporated as a reference) in TN buffer. A sample volume of about 200 µl was layered on 300 µl 15% saccharose containing 1% Triton X-100 in TN and a 12 ml saccharose gradient in TN from 20 to 50% by weight containing 0.2% by weight Quil A. The centrifuging was carried out at 250,000 g for 22 hours at 20° C. After centrifuging, fractions of 500 μl were collected from below and samples (20–50 μl) were measured for radioactivity. The radioactive protein fractions were put together and dialyzed on 0.005 m Tris-HCl, 0.01M NaCl, pH 7.4, was dosed in 10 ml flasks and concentrated by lyophilisation for 18 hours in an Edwards freeze-drying apparatus.

This preparation has a sedimentation coefficient of 24 S.

Further purification of the complex was done by centrifuging of the complex through a 10–40% by weight saccharose gradient.

EXAMPLE 2

The process according to Example 1 was repeated by using equine influenza visus (Solvalla, isolated from Solvalla, Stockholm). The experiment was repeated without glycoside being added (i.e. in principle according to EPC application No. 81102213.6) and the protein micelles so obtained and the protein complex produced with glycoside were subjected to sedimentation gradient centrifuging through a 10–40% by weight sugar solution at 280,000 g for 4 hours at +4° C. The results are given in FIG. 1 which also shows the sedimentation coefficient for tyroglobulin as standard (19 S at the arrow). It reveals that the sedimentation coefficient for protein micelles is 30 S and for glycoside protein complex 19 S. (The virus glycoprotein was marked with galactosoxidase-$^3$H-borhydride method.)

EXAMPLE 3

Figure 2:
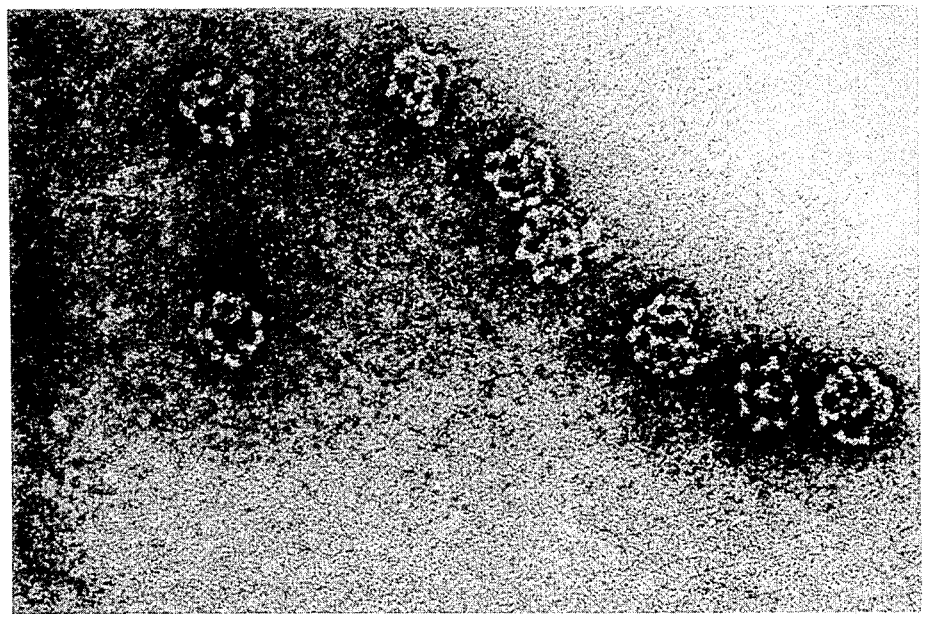

The process according to Example 1 was repeated with measles virus instead of parainfluenza-3-virus. A complex was obtained which under electromicroscopy showed the characteristic structure revealed in FIG. 2.

EXAMPLE 4

Rabies virus, produced at RIV, Bilthoven, according to the method described by Van Wezel et al. (Develop. Biol. Standard (1978), 41, 159–168) was concentrated to 2 mg/ml in TN 1 mg of virus was made soluble with 100 mM octyl-β-D-glucoside and was incubated for 45 minutes at 20° C. The sample was layered over a 50% by weight sugar solution and was centrifuged at 250,000 g for 45 minutes at +4° C. The upper solution was extracted and Quil A was added to 0.2% by weight.

The sample was enclosed in a cellulose hose and dialyzed at +20° C. in 0.15M ammonium acetate buffer in a volume of 1000 ml, which was changed 3 times during 72 hours of constant agitation. The dialyzed material contained rabies virus complex. A portion of the material was purified further by means of centrifuging through a 10–40% by weight sugar solution at 280,000 g for 4 hours at +4° C. Electron microscopy revealed the structure shown in FIG. 3.

EXAMPLE 5

The process according to Example 4 was repeated with measles virus. The complex obtained showed the same structure as the complex produced according to Example 3.

EXAMPLE 6

Parainfluenza-3-virus (U-23) was purified with saccharose gradient centrifuging and virus thus purified was dissolved to a concentration of 10 mg/ml in 0.02M barbiton buffer, pH 8.0, 0.24M glucose (BG). 1–5 mg/ml PI-3-virus in BG-buffer, was made soluble with 2% Triton X-100 together with about $10^5$ $^3$H-counts/minute-marked virus (according to ref Luukkonen et al, 1977) in BG-buffer. A sample volume of 1 ml was layered on a 1% agarose gel containing 0.02M barbiton buffer, pH 8.0, and 0.02% by weight Quil A. The agarose gel was enclosed in a tube with a surface of 85 mm$^2$ and a height of 25 mm. The upper position and the lower portion of the tube were each connected to electrophoresis buffer of 0.02M barbiton buffer, pH 8.0. The upper vessel was connected to a negative electrode and the under vessel to a positive electrode. The electrophoresis was carried out at 5 V/cm for 4 hours. The sample was collected on the anode side of the gel and it was measured for radioactivity. The sample was dialyzed in 0.15M ammonium acetate buffer, pH 7.0, and was concentrated by lyophilization.

This preparation had a sedimentation coefficient of about 20 S, measured in the same manner as in Example 2.

Further purification of the complex was done by centrifuging the complex through a 10–40% by weight saccharose gradient.

EXAMPLE 7

*Toxoplasma gondii* (obtained from Tage Waller, Statens Veterinärmedicinska Anstalt) was purified by means of filtering through cotton and centrifuging through 30% by weight saccharose at 100,000 g for 20 minutes at 4° C. The purified preparation was dissolved to a concentration of about 5 mg/ml in 0.05M Tris-HCl, pH 7.4, and 0.1M NaCl (TN). 1 mg of *Toxoplasma gondii* was solubilized in 5% octyl-β-D-glucoside and 5% saponin according to "An investigation of the antigenic structure of *Toxoplasma gondii*", Parasite Immunology 1981, 3, 235–248, incorporated as a reference, together with about $10^5$ counts/minute $^3$H-marked toxoplasmas (Luukkonen et al, 1977) in TN-buffer. A sample volume of about 200 μl was stratified over 300 μl of 15% saccharose containing 1% Triton X-100 in TN and a 12 ml saccharose gradient in TN from 20 to 50% by weight containing 0.2% by weight Quil A. Centrifuging was done at 150,000 g at 20° C. for about 18 hours. After centrifuging, the gradient was drawn off in fractions of 500 μl and samples of (20–50 μl) were measured for radioactivity. Two different radioactive peaks could be detected. The fractions within the various peaks were put together, each peak by itself, were dialyzed and concentrated by freeze-drying as disclosed in Example 1. The complex with Quil A had a lower sedimentation coefficient than protein micelles produced from the same parasite.

EXAMPLE 8

Bacteria *E. coli* with plasmid pili K 88 were shaken mechanically and precipitated three times at the isoelectric point. The material was then treated in the same manner as described in Example 1. Complexes were obtained with the characteristic structure shown in FIGS. 2 and 3.

EXAMPLE 9

The process according to Example 8 was repeated with Salmonella, which carries porin protein. Complexes were obtained with the characteristic structure shown in FIGS. 2 and 3.

EXAMPLE 10

Epitel kidney cells from cats which had been infected by Feline leukemia virus were treated with the process according to Example 1. Complexes were obtained with the characteristic structure revealed in FIGS. 2 and 3.

EXAMPLE 11

Epitel kidney cells which had been transformed by bovine leukemia virus were treated with the process according to Example 1. Complexes were obtained with the characteristic structure shown in FIGS. 2 and 3.

EXAMPLE 12

Parainfluenza-3-virus U-23 was purified and protein complex was prepared according to the process of Example 1 but with the difference that saccharose gradient in TN from 20 to 50% by weight contains a saponin other than Quil A. Two commercially available saponins were tested, Merck "Weiss", rein 51400023 and Sc, Lickhardt "S" Schuchardt, Munich. (Saponins in pure form. The manufacturer did not want to reveal the type of the product. In thin layer chromatography they differ from Quil A). The resulting complex had a sedimentation coefficient of 24 S and showed the same structure as that of the complex prepared according to Example 3.

EXAMPLE 13

5 mg measles virus were solubilized according to Example 3 and applied to an anion exchanger of DEAE cellulose type. The ion exchanger was kept in a column of 20 ml and was equilibrated with 0.01M phosphate buffer, pH 7.2, 0.5% by weight of octyl-$\beta$-D-glucoside. The sample material was applied to the ion exchanger and non-adsorbed material was washed away after rinsing-through by 5 column volumes 0.01M phosphate buffer, pH 7.2, 0.5% by weight of octyl-$\beta$-D-glucoside, and then the adsorbed material was eluted after addition to the column of a salt gradient between 0 and 0.5M NaCl dissolved in 0.01M phosphate, pH 7.2, 0.5% by weight of octyl-$\beta$-D-glucoside. The fractions in which measles membrane proteins were identified were combined and Quil A was added to 0.1% by weight and dialyzed on 0.05M ammonium acetate, pH 7.0. A complex was formed with the characteristic structure in FIGS. 2 and 3.

EXAMPLE 14

22 nm particles of Hepatitis B virus received from London School of Tropical Medicine and Hygiene (England) was resuspended to a concentration of 1 mg/ml in TN. 0.3 mg protein of 22 nm particles were solubilized by 2% by volume of Triton X-100, 0.5M NaCl and incubated for 16 hours at $+37°$ C. Then the process according to Example 1 was repeated. The resulting complex showed a sedimentation coefficient of 20 S. Electron microscopy revealed a complex having a structure as that shown in FIG. 4. This structure differs from the structure shown in FIG. 2 in that it consists of parts of this structure.

EXAMPLE 15

3 mg bovine diarrhoea virus (B DV) dissolved in TN, were solubilized by addition of Triton X-100 to 1% by volume. The mixture was agitated for 2 hours at room temperature. Thus solubilized virus was applied to a lectin column consisting of the lectin Lentil immobilized to Sepharose 4 B (Pharmacia, Uppsala). The column was equilibrated with TN and after introduction of the virus material on to the column, it was washed with 5 column volumes TN containing 0.1% by volume Triton X-100 followed by 10 column volumes TN. Virus enveloped proteins were desadsorbed by eluting buffer consisting of 0.2M methyl-$\alpha$-D-mannoside, 0.5% by weight of octyl-$\beta$-D-glucoside dissolved in TN being added to columns. The fractions containing virus enveloped proteins were collected and Quil A was added to 0.1% by weight. The mixture was dialyzed on 0.05M ammonium acetate pH 7.0 at $+4°$ C. for 3 days with three changes of buffer volume of 1 liter.

Figure 4:
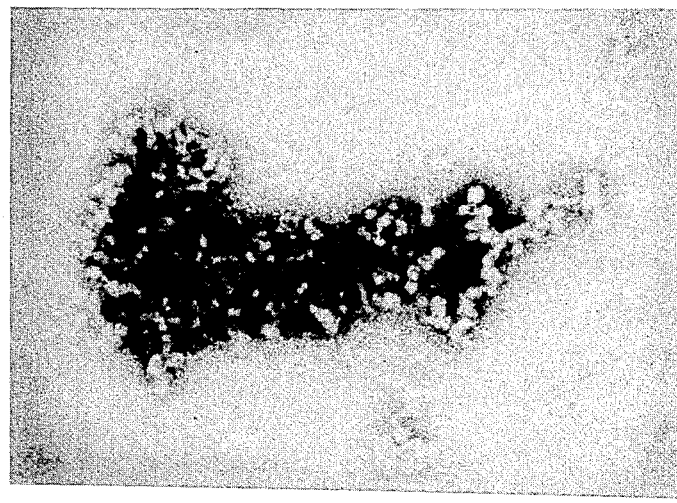

The final product was subjected to lyophilization and electron microscopy revealed (complex) structures being parts of the complex shown in FIG. 4. This preparation had a sedimentation coefficient of 20 S.

EXAMPLE 16

Polio virus was killed by formalin and purified by known methods for example by ultrafiltration followed by gel chromatography in Sepharose (Pharmacia, Uppsala), and finally density centrifugation in ceasium chloride.

Virus was solubilized in a suitable solubilizing buffer such as TN containing a solubilizing agent i.e. 2% SDS (Sodium Dodecyl Sulphate) which is heated to 90° C. for 2 minutes. The virus proteins are separated by electrophoresis in a 13% polyacrylamide gel containing 0.1% SDS. The proteins in the gel were identified after colouration with Co massie Blue R 250. VP 3 was one of the virus proteins having a molecular weight of about 26 000 dalton. This virus protein strand was cut out from the gel and extracted therefrom by transverse electrophoresis.

Figure 3:
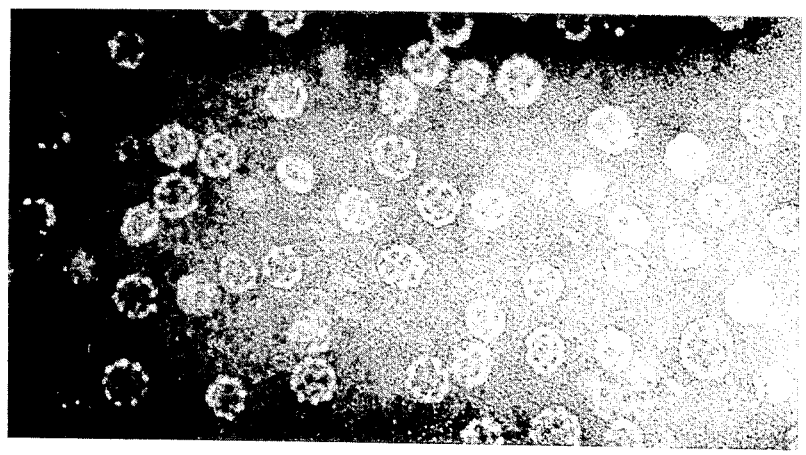

The extracted material was dissolved in TN containing the solubilizing agent 2% Triton X-100. This mixture was then used to produce protein complex (iscomer) according to the centrifuging method, see Example 1. Electron microscopy revealed the characteristic structure of the preparation as shown in FIG. 3.

EXAMPLE 17

Purified killed poliovirus, produced at the RIV, Bilthoven, was dissolved in 67% by volume of acetic acid containing 0.1M MgCl$_2$.

The virus material was then subjected to ultra-centrifugation for 2 hours at 100,000 g, and the supernatant containing solely virus proteins was taken care of and dialyzed in the presence of 0.1% by weight Quil A against 0.01M Tris, 0.14M NaCl, pH 7.4. The resulting complex showed the same structure as that of the complex prepared according to Example 3.

EXAMPLE 18

Outer membrane proteins of *Neisseria meningitidis* were received freeze-dehydrated from National Institute of Health, the Netherlands, and were dissolved in TN containing 2% by weight octyl-$\beta$-D-glucoside and 0.1% by weight Quil A, and treated in the same manner as in Example 4. The resulting complex had a sedimentation coefficient of 20 S measured in the same manner as in Example 2.

EXAMPLE 19

Peptide with hydrophobic amino acids. Foot-and-mouth disease peptide 144–169, O Kaufbehren. VP 1 synthezided with 0, 1, 2, 3 and 4 Tyrosin, coupled to one end, was used (as commercially received). The peptide was dissolved in an exceedingly small amount of 67% by volume of acetic acid, neutralized with 25% ammonia and diluted to 0.5M Amm Acetate with Ag dest (detergent to 2% final concentration). 0.1% glycoside was added and the mixture was dialyzed against 0.05M Amm Acetate, pH 7. (Dialysis tube Spectra Por 6 MWCO 1.000).

Mice were vaccinated twice with 50 μg at intervals of 2 weeks.

| Peptide/number Tyr | ELISA value (antibodies) 2nd tapping |
|---|---|
| 0 | 0.005 |
| 1 | 0.217 |
| 2 | 0.311 |
| 3 | 0.347 |
| 4 | 0.346 |

Complex having formed can be shown by electron microscopy (see FIG. 5) revealing a spherical electron tight particle having a length 20–40 nm and a breadth 10 nm. Other sizes were also seen.

Figure 5A:
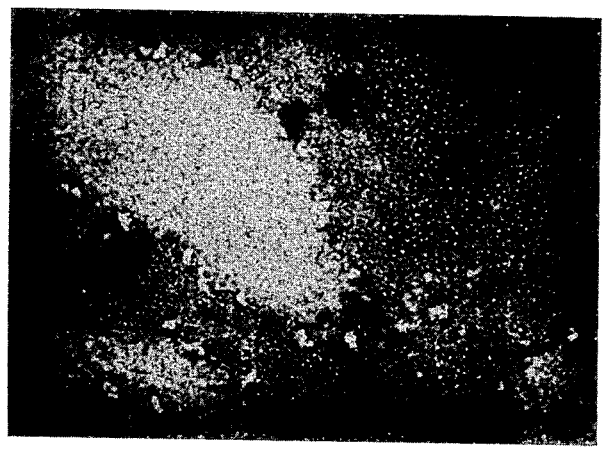
Figure 5B:

FIG. 5a shows the electron microscope (EM) picture of the peptide coupled to three tyrosine and FIG. 5b shows the EM picture of the peptide coupled to four tyrosine.

EXAMPLE 20

IgG from mice, purified according to known methods (M Van den Branden, J L de Coen, L Kanarek and Ruyschaert (1981) and Molecular Immunology 18, pp 621–631 (1981)) or enriched by ammonium sulphate solution (J E Conradie, M Govender, L Visser, Journal of Immunological Methods Vol 59, pp 289–299, 1983, citations incorporated as reference) was dialyzed overnight against 1 liter 0.15M phosphate citrate (PC buffer pH 2) in refrigerating chamber. 2% detergent (e.g. octyl-β-D-glucoside) was then added. If a detergent having a low critical micellar concentration (CMC) is used, the detergent should be changed before starting dialysis. The mixture was dialyzed against PC pH 7. One hour later Quil A was added to a final concentration of 0.05%, and the dialysis was continued on PC pH 7 for 24 hours in refrigerating chamber.

Complex forming was shown by centrifuging through a 5 to 30% saccharose gradient for 3.3 hours at 40 000 rpm in a Beckman SW-60 rotor. The complexes were detected in the gradient by means of ELISA technique.

EXPERIMENT 1

A comparison between the immunogenic effect of the membrane protein complex produced with Quil A according to the invention and corresponding membrane protein micelles produced without glycoside addition.

25 mice (BALB C, Bomhollgard, Denmark, weight about 20 g) were divided into 5 groups and the groups were immunized twice at three week interval with only buffer solution (PBS) 0.1 μg, 0.5 μg and 5 μg of the complex produced with membrane proteins from influenza and Quil A in 100 μl PBS according to Example 1, and with 5 μg membrane protein micelles without glycoside, made according to EPC Application No. 81102213.6.

Serum was collected each week from the mice until the end of the experiment. The immune response was measured in serum with the ELISA technique. Voller, Bidwell and Bartlett 1980, Enzyme-linked Immunosorbent Assay, pp 359–371, in the Manual of Clinical Immunology, American Society for Microbiology, Washington.

Figure 6:
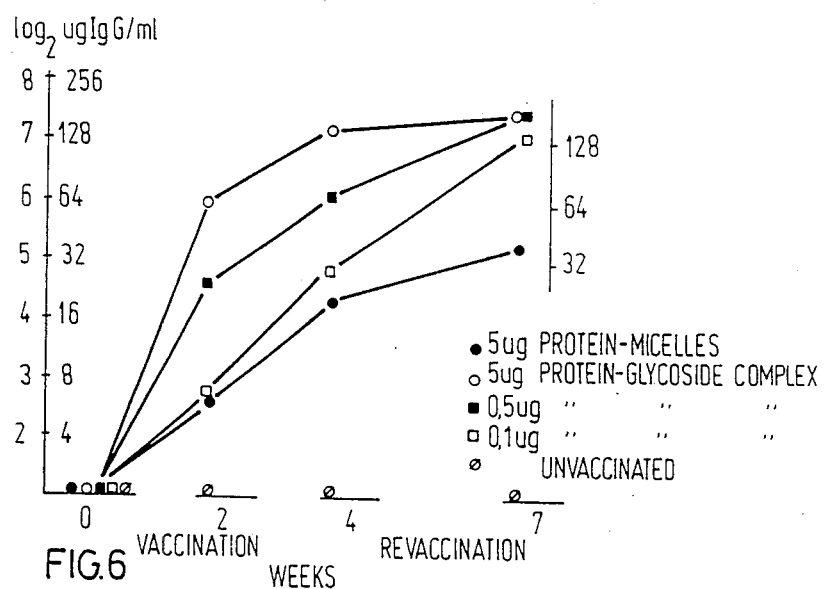

The results are shown in FIG. 6. It is evident that the antigenic complex produced with Quil A provides a better immune response than the corresponding protein micelles without the addition of Quil A. 0.1 μg of the protein membrane complex made with Quil A induces a higher immune response than 5 μg of the protein micelles without addition of the glycoside.

EXPERIMENT 2

Comparison between immunogenic effect and side effects of membrane protein complex produced with Quil A according to the invention and corresponding membrane protein micelles mixed with the glycoside as adjuvant additive.

30 guinea pigs from The National Veterinary Institute, Sweden breeding were used in the experiment. They were distributed into five groups of six animals and vaccinated with protein micelles (P) from influenza virus (culture Solvalla) and with membrane protein complexes from the same influenza virus produced with glycoside Quil A (GP) according to Table 1. Preparation according to Example 2. Six guinea pigs were included as an unvaccinated control. The GP complexes had been freed of free glycoside by saccharose gradient centrifuging. The results are revealed in Table 1. P-micelles as well as GP-complexes produce minimal reactions and GP-complexes appreciably higher antibody responses than P-micelles. Mixture of 10 μg free glucoside with P-micelles produces mild reactions but no adjuvant effect. Addition of 100 μg free glycoside produces strong local reactions in the form of redness and swelling and a higher antibody response than P-micelle vaccine.

TABLE 1

The immune response to influenza virus in guinea pig serum measured with haemagglutination inhibition (HI)-test after two vaccinations with an interval of 4 weeks. Serum is taken 10 days after the second vaccination.
P = 1 μg protein micelle consisting of influenza virus peplomers (H and N).
P + 10 = 1 μg protein micelles + 10 μg free glycoside.
P + 100 = 1 μg protein micelles + 100 μg free glycoside.
GP = 1 μg protein complex produced with glycoside containing <0.1 μg free glycoside.
− no reaction
+ slight redness
++ moderate redness
+++ strong redness and necroses

| HI-titres ($^2$log/l) | P | P + 10 | P + 100 | GP |
|---|---|---|---|---|
| M ± SD 6 animals | 7.9 ± 2.3 | 7.5 ± 1.5 | 10.3 ± 3.1 | 9.7 ± 0.6 |
| Local reaction | − | + | +++ | − |

1 Non-vaccinated guinea pigs had titres 2 (6 animals)

EXPERIMENT 3

Membrane protein complexes produced according to Example 1 and further purified by centrifuging through 10–40% saccharose gradient were tested for immunogenic effect. This preparation has no demonstrable amounts of free Quil A (<0.02% by weight) measured with a method based on Quil A's lytic activity. The lytic activity was investigated for bovin red blood corpuscle. The blood corpuscles were held in an agarose gel with a concentration of 0.05%. The agrose gel was placed in an electrophoretic system in which Quil A moves towards the anode and lyse the blood cells. The lysed zone has the form of a rocket and the amount of glycoside is proportional to the length of the rocket and is made visible by protein dying with Coomasie Brilliant Blue. This method can determine a concentration of 0.02% glycoside or more (Sundqvist et al, Biochemical and Biophysical Research Communications Vol 114, pp 699–704, 1983).

In sedimentation rate analysis, the additionally purified material has the same sedimentation coefficient as the non-purified material. Electron microscopy revealed particles with the same morphology (see FIGS. 2 and 3). For vaccination with mice, the material was an active as non-purified material in stimulating antibody response. In an experiment, 1 μg of 0.1 μg complex of influenza virus protein complex prepared with Quil A-addition, purified by two gradient centrifugings according to the above, was as effective as the corresponding material which was further purified. The above result shows that the complexes are stable and effectively immunogenic without any demonstrable amounts of free Quil A.

EXPERIMENT 4

Three different vaccines with Hepatitis Bs (HBs) antigen were tested respectively on 4 mice with a dose of 5 μg HBs antigen. The three vaccines were iscomes prepared according to Example 14, intact 22 nm particles corresponding to a commercially available vaccine and an experimental vaccine in which corresponding HBs proteins are present in the form of micelles prepared according to EPC Application No. 81102213.6. The antibody response has been estimated by ELISA methods.

TABLE 2

| | VACCINE | | |
|---|---|---|---|
| | iscomer | 22 nm particles | micelles |
| ELISA extinction value read at 495 nm | 1.343 | 0.603 | 0.569 |
| | 1.788 | 0.598 | 0.240 |
| | 1.841 | 0.888 | 0.273 |
| | 1.884 | 0.892 | — |

Table 2 shows that mice immunized by iscoms responded by considerably higher antibody titres than HBs vaccines containing intact 22 nm particles or micelles.

EXPERIMENT 5

In a vaccination experiment followed by challenge with a pathogenic rabies strain (CVS) iscoms, prepared according to Example 4, containing enveloped proteins from rabies virus have been tested on mice as to the capability of causing protective immunity. The mice were vaccinated once with a dose according to Table 3. The mice were test-infected 14 days later with the mice pathogenic CVS strain.

TABLE 3

| Vaccination dose (μg) | Surviving/total number of animals |
|---|---|
| 4.2 | 18/19 |
| 0.84 | 15/18 |
| 0.17 | 10/20 |
| — | 0/20 |

The table shows that the iscom vaccine causes protective immunity.

The new antigenic complexes according to the invention can be stored as lyophilisated preparations or as aqueous suspensions. For administration, they are suitably in a solvent such as e.g. physiological salt solution. Preferably, 0.1M NaCl solution, pH 7.2–7.6, is used. The pH-value is adjusted by 0.05M Tris-HCl. Other buffers can also be used.

The new protein complexes according to the invention have a stronger immunogenic effect—about 10 times and often more—than protein micelles which are not produced with glycoside, and which have not been mixed with any adjuvant. If the corresponding protein micelles are to have the same immunogenic effect at the same protein dose, they must be mixed with so much glycoside or other adjuvant that the side effects will be much too great.

The protein complexes according to the invention do not need to be mixed with any adjuvant and thus the side effects are minimized. Furthermore, the new complexes are stable in contrast to antigenic proteins bound to liposomes.

I claim:

1. Immunogenic complex containing antigenic proteins and peptides with hydrophobic regions and at least one polar triterpensaponin having hydrophobic regions, said complex being formed by attraction between said hydrophobic regions of said at least one polar triterpensaponin and said hydrophobic regions of said proteins and peptides, said complex being obtained by mixing proteins, peptides, viruses, mycoplasmas, bacteria, parasites or animal cells with hydrophobic regions with one or more solubilizing agents, whereby complexes are formed between charged monomeric antigenic proteins or peptides and solubilizing agent, whereafter the charged monomeric antigenic proteins or peptides are separated from solubilizing agent in the presence of, or are separated from the solubilizing agent and directly transferred to a triterpensaponin solution, containing one or more triterpensaponins with hydrophobic and hydrophilic regions in a concentration of at least the critical micellular concentration.

2. Immunogenic complex according to claim 1, wherein said complex has a lower sedimentation constant than the corresponding protein or peptide micelles and a higher sedimentation constant than the corresponding monomeric form of protein or peptide.

3. Immunogenic complex according to claim 1, wherein said complex has an open spherical structure consisting of circular subunits or parts of the spheric structure.

4. Immunogenic complex according to claim 1, wherein the proteins and peptides are selected from the group consisting of (A) amphiphatic proteins and peptides with hydrophilic and hydrophobic groups derived from or being membrane proteins or membrane peptides from enveloped viruses, bacteria, mycoplasmas, parasites or animal cells, or such proteins or peptides produced by hybrid DNA tecnique, or molecules produced synthetically, (B) hydrophilic proteins and peptides made amphiphatic by hydrophobic groups being coupled to them; these proteins or peptides may derive from viruses, bacteria, mycoplasmas, parasites, or be synthesized or obtained by hybrid DNA technique, (C) amphiphatic proteins and peptides obtained by rendering inaccessible hydrophobic parts of hydrophilic proteins accessible by chemical means; these proteins may derive from the microorganisms or cells mentioned above or obtained by hybrid DNA techniques, or be synthesized.

5. Immunogenic complex according to claim 4, in which the proteins and peptides are chosen from the group consisting of amphiphatic proteins and non-hydrophobic proteins from viruses, mycoplasmas, bacteria, parasites, animal cells whose non-hydrophobic proteins have been rendered hydrophobic by coupling of hydrophobic groups thereon, which hydrophobic groups are selected from the group consisting of aliphatic groups with 1–8 carbon atoms, small peptides with 1–5 amino acids, choline acid and cholesterol derivatives; amphiphatic proteins and peptides containing non-accessible hydrophobic groups, that have been made accessible through gentle denaturation; or synthetic proteins or peptides or proteins or peptides produced by hybrid DNA technique.

6. Immunogenic complex according to claim 4 in which the proteins and peptides are selected from the group consisting of Orthomyxoviridae, Paramyxoviridae, Retroviridae, Rabdoviridae, Coronaviridae, Togaviridae, Herpesviridae, Bunyaviridae, Hepatitis B virus, membrane proteins from toxoplasma, Picornaviridae, Parvoviridae and Reaviridae.

7. Immunogenic complex according to claim 1 in which the triterpensaponin is a glycoside extract from *Quillaja saponaria molina, Aesculus hippocastanum* or *Gyophilla struthium*.

8. An immunogenic pharmaceutical composition containing an immunogenic-effective amount of a complex according to claim 1, in admixture with a pharmaceutically acceptable excipient.

* * * * *